United States Patent
Marsala et al.

(10) Patent No.: US 6,435,021 B1
(45) Date of Patent: Aug. 20, 2002

(54) PROCESS FOR VERIFYING THE EFFECTIVENESS OF DRILLING FLUIDS IN STABILIZING OIL WELL WALLS

(75) Inventors: Alberto Marsala, Bergamo; Lucilla Del Gaudio, San Donato Milanese; Stefano Carminati, Monza, all of (IT)

(73) Assignees: ENI S.p.A., Rome; Enitecnologie S.p.A., San Donato Milanese, both of (IT)

( * ) Notice: Subject to any disclaimer, the term of this patent is extended or adjusted under 35 U.S.C. 154(b) by 0 days.

(21) Appl. No.: 09/721,766

(22) Filed: Nov. 27, 2000

(30) Foreign Application Priority Data

Nov. 26, 1999 (IT) .................................... MI99A 002474

(51) Int. Cl.$^7$ ............................................. E21B 49/00
(52) U.S. Cl. .................................................. 73/152.23
(58) Field of Search ........................ 73/152.23, 152.52, 73/152.53, 788, 38; 175/50; 166/250.1

(56) References Cited

U.S. PATENT DOCUMENTS

| | | | |
|---|---|---|---|
| 5,345,819 A | 9/1994 | Dearing, Jr. | ............. 73/152.23 |
| 5,511,615 A | 4/1996 | Rhett | ....................... 166/250.1 |
| 5,679,885 A | 10/1997 | Lenormand | ..................... 73/38 |
| 5,741,971 A | 4/1998 | Lacy | ............................ 73/597 |

Primary Examiner—Hezron Williams
Assistant Examiner—Jay L Politzer
(74) Attorney, Agent, or Firm—Oblon, Spivak, McClelland, Maier & Neustadt, P.C.

(57) ABSTRACT

Process for measuring the effects on the mechanical properties of shales due to interaction with drilling fluids, which comprises:

(a) preparation of a shale sample;

(b) measurement of the transmission velocity of ultrasonic waves through the sample (a), (c) preparation of a mixture of water-or oil-based drilling fluid and the sample (a);

(d) removal of the shale sample (a) from the mixture (c) and measurement of the ultrasonic wave transmission velocity;

(e) comparison between the measurements of step (d) and those of step (b).

3 Claims, 1 Drawing Sheet

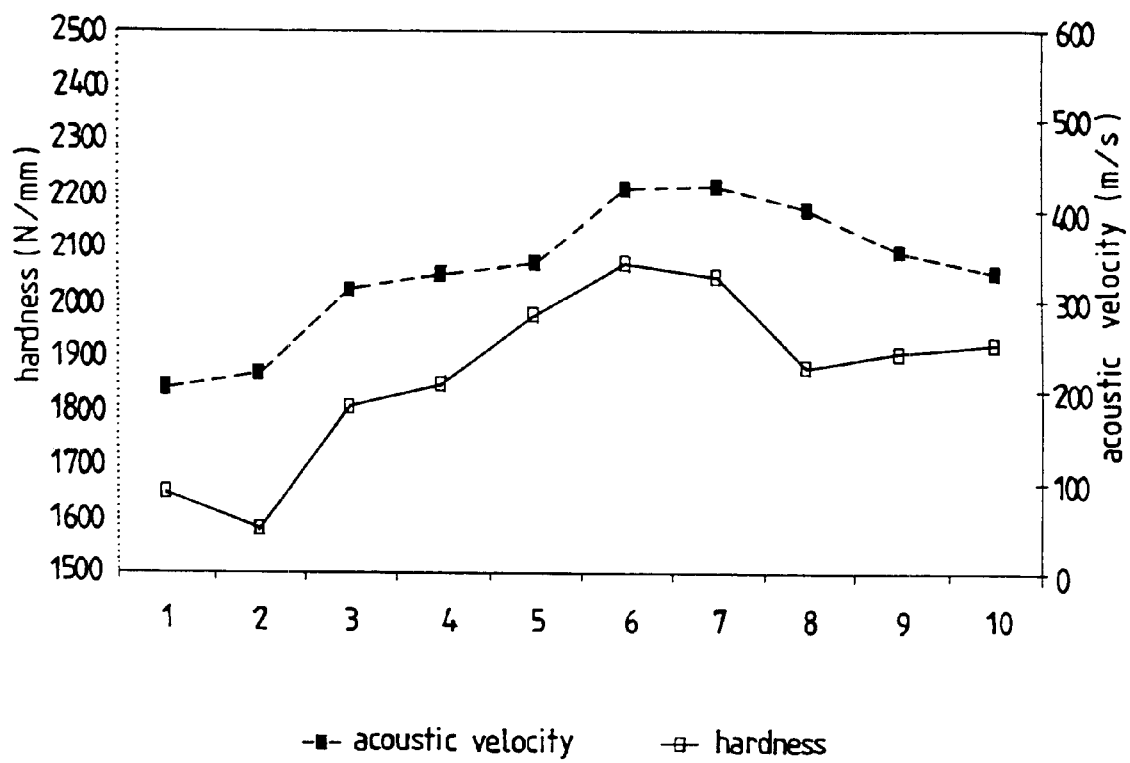

PROCESS FOR VERIFYING THE EFFECTIVENESS OF DRILLING FLUIDS IN STABILIZING OIL WELL WALLS

The present invention relates to a process for verifying the effectiveness of drilling fluids in stabilizing oil well walls, by measuring the ultrasonic wave transmission velocity on clay cuttings subjected to aging in drilling fluids.

During drilling of an oil well, there is often the problem of instability of the well in shale formations. To prevent this instability, drilling fluids are prepared with additives suitable for inhibiting shale swelling.

The effectiveness of these additives is evaluated by tests which are specified in API procedures, for example, dispersion tests of clay cuttings in mud (hot-rolling test) or laboratory procedures (for example measuring the swelling of clay samples).

None of these techniques used in the prior art takes into account the mechanical characterization of the shale, one of the main factors in determining the effect of the drilling fluid on the stability of the well walls.

On the other hand, techniques for evaluating the mechanical characteristics (for example uniaxial, triaxial, indentation tests) have the great disadvantage of being destructive, costly and time-consuming.

It is also known that the related mechanical properties can be discovered from measuring the velocity of sound waves through rock samples. Although these acoustic techniques are not destructive, they have the drawback of being used at present only for the acoustic characterization of formations that gives the mechanical properties of the rock. They neglect, on the other hand, the effect due to rock-drilling fluid interaction.

A process has now been found which overcomes the above disadvantages as it allows the mechanical properties of shales to be evaluated in the presence of drilling fluids. The process of the present invention also has the advantage of not being destructive.

In accordance with this, the present invention relates to a process for measuring the effects on the mechanical properties of shales due to interaction with drilling fluids, which comprises:

(a) preparation of a shale sample having at least two flat, parallel opposite surfaces;

(b) measurement of the transmission velocity of ultrasonic waves through the sample of step (a), (c) preparation of a mixture of water-or oil-based drilling fluid and the shale sample (a);

(d) removal, after a pre-established time, of the shale sample (a) from the mixture (c) and measurement of the ultrasonic wave transmission velocity through the sample thus removed;

(e) comparison between the measurements of step (d) and those of step (b).

The process of the present invention can be applied to cuttings produced during drilling, or to samples prepared from outcrop shale or cores.

Alternatively, it is possible to operate on reconstituted shale samples.

When cuttings produced during drilling are used, owing to their irregular geometry, they must be subjected to smoothing or grinding until two flat, parallel surfaces are obtained. This can be achieved by smoothing each cutting by means of diamond sandpaper disks lubricated with oil or demineralized water, until two flat, parallel surfaces are obtained.

Step (a) of the process of the present invention consists in the preparation of shale. This is done preparing suitably-sized (at least 2 mm thick) test-samples. When cuttings are used, these can either derive from wells or be prepared from cores (well or quarry). The sample preparation is normally carried out with an automatic slitter in demineralized water or oil to obtain the desired test-samples, which must have at least two flat, parallel surfaces. Samples that have cracks are discharged. It is essential for them not to be exposed to the air as the response of the sample greatly depends on the degree of saturation.

Step (b) consists in measuring the sound wave transmission velocity through the shale sample. The test consists in generating an ultrasonic pulse by means of an emitter transducer (connected to a function generator) onto a surface of the sample and recording, by means of an oscilloscope (connected to a receiver transducer), the transit time t of said pulse through the sample. If the thickness of the sample L is known, the sound disturbance velocity is given by the ratio $V=L/t$.

The fact of generating compressional or shear waves is related to the particular type of transducers used; in particular a pair of transducers (emitter and receiver) is used for compressional waves and a pair of transducers (emitter and receiver) for shear waves. The ultrasonic wave passes through the sample and is converted to an electric signal by the receiver transducer; the electric signal received is then visualized by means of a digital oscilloscope which, taking into account the delay due to the transducers and circuit, enables the transit time of the ultrasonic pulse through the cutting to be determined.

If the thickness of the cutting is known, it is thus possible to determine the transmission velocity of the compressional or shear ultrasonic waves.

The water-or oil-based drilling fluids used in step (c) are well-known to experts in the field (see for example Gray G. R. and Darley H. C. H.: "Composition and properties of oil well drilling fluids"; Gulf Publishing Company, fourth edition, Houston Tex. U.S.A., 1980).

Step (c) consists in the preparation of the mixture of shale (a) and drilling fluid. This mixture, preferably prepared by pouring the shale (a) into the drilling fluid, is brought at the desired temperature, indicatively from 10° C. to 200° C., preferably from 20° C. to 150° C. The mixture thus prepared is left to age either under static conditions or under stirring.

After a pre-established time, shale samples are removed from the shale/drilling fluid mixture (step d). Measurements of the compressional and shear wave velocity through the cutting are then taken, care being taken not to let it dry. The procedure is identical to that of step (b). In order to allow acoustic coupling, however, a particular coupling fluid is inserted between transducers and sample. These fluids preferably have viscosity values ranging from 200 to 800 poises measured with a shear velocity gradient of $3.1\ s^{-1}$ (Standard American Petroleum Institute 13 B-1).

The above technique, also known as "pulse velocity" can be used on cores (for example cylindrical rock samples having a diameter of 2.5 cm and double the height), but also on rock fragments with dimensions of less than a centimeter which reach the surface during drilling.

The experimental apparatus generally consists of (a) a pulse generator with a duration time varying from 1 $\mu s$ to 20 $\mu s$; (b) a pair of piezoelectric transducers capable of generating compressional ultrasonic waves, highly damped and with a 100% band width or, alternatively, a pair of piezoelectric transducers capable of generating shear ultrasonic waves, highly damped and with a 100% band width; (c) a digital oscilloscope with a minimum resolution of $10^{-2}\ \mu s$.

In particular, it is known that the compressional wave velocity $V_p$ through a material is directly proportional to the Lamè $\lambda$ constant and shear modulus G and inversely proportional to the density of the material $\rho$, according to the equation: $V_p=\sqrt{(80+2G)/\rho}$.

Analogously, it is known that the shear wave velocity $V_s$ is directly proportional to the shear modulus G and inversely proportional to the density of the material $\rho$, according to the equation: $V_s=\sqrt{G/\rho}$.

In addition, it is known that the Lame $\lambda$ constant is in relation to the bulk modulus of elasticity K of a material by means of the equation $\lambda=K-2\cdot G/3$.

The bulk modulus K is also intended as the inverse of the compressibility, as a result of which an analysis of the ultrasonic wave transmission velocity through a shale sample makes it possible to determine the effects due to interaction with a fluid on the mechanical properties (compressibility, shear modulus) and on the density of the material. These properties are in fact key parameters which indicate the capacity of a shale formation of not generating instability phenomena during well drilling.

The process of the present invention has the great advantage of not being destructive, although providing the same results as the destructive methods of the prior art.

The following examples are provided for a better understanding of the present invention.

EXAMPLES

Acoustic velocity measurements are specified on cuttings of outcrop shale aged in different drilling fluids for 12 days at 80° C., whose composition is indicated in Table 1. A saturated outcrop shale was used (Pierre Shale 2) coming from South Dakota. The additives used in the formulation of the drilling fluid, indicated below, were subdivided into use classification.

Clay Inhibitors
** Avasilix® 22, AVA: sodium silicate (Silicate-Na);
** Soltex®, AVA: modified asphaltene (Soltex-Na);
** KCl
Dispersing Agent
** Rheomate®, Lamberti: Zirconium citrate (ZRC)
Filtrate Reducer
** PAC-LV, Baroid: polyanionic cellulose
Lubricant
** Avagreen Biolube, AVA: ester.

The table indicates the compositions of the solutions in which the Pierre Shale 2 cuttings were aged for 12 days at 80° C. and the results of the acoustic measurements on different shale cuttings after aging. Different acoustic velocity values can be found for cuttings aged in different formulations, indicating different mechanical effects induced by rock-fluid interaction. The velocity of the various cuttings before aging, on the other hand, is constant as they derive from the same sample of Pierre Shale 2.

| Sample # | Composition (concentration additives in wt %) | | | | | | Sound velocity (m/s) |
|---|---|---|---|---|---|---|---|
| | silicate-Na | soltex-Na | ZRC | pac-1v | ester | KCl | |
| 1 | 0 | 0 | 0.6 | 1 | 0.4 | 0 | 1842 |
| 2 | 0 | 6 | 0 | 0 | 0 | 0 | 1869 |
| 3 | 0 | 6 | 0 | 1 | 0 | 10 | 2020 |
| 4 | 0 | 6 | 0.6 | 0 | 0.4 | 10 | 2046 |
| 5 | 10 | 0 | 0 | 0 | 0 | 0 | 2066 |
| 6 | 10 | 0 | 0 | 1 | 0.4 | 10 | 2203 |
| 7 | 10 | 0 | 0.6 | 0 | 0 | 10 | 2210 |
| 8 | 10 | 6 | 0 | 0 | 0.4 | 10 | 2168 |
| 9 | 10 | 6 | 0 | 1 | 0.4 | 0 | 2091 |
| 10 | 10 | 6 | 0.6 | 0 | 0 | 0 | 2052 |

Example 2

The figure indicates for comparative purposes, the acoustic velocity values of example 1 and the hardness values obtained with a destructive test, i.e. with the indentation test, on the same samples following sonic measurement [the indentation test is carried out by measuring the force applied to a point with a diameter of 1 mm to penetrate the shale by 0.3 mm at a rate of 0.01 mm/s and gives a direct indication of the rock hardness, and consequently of the mechanical stability of the shale formation].

A good correspondence is observed between acoustic velocity and hardness of the cutting for the various samples aged in the solutions specified in the table. This indicates that the acoustic velocity measurements can be used to evaluate the mechanical characteristics of shale and consequently evaluate the impact of the drilling fluid on the stability of the drilling well walls.

What is claimed is:

1. A process for measuring the effects on the mechanical properties of shales due to interaction with drilling fluids, which comprises:

(a) preparation of a shale sample selected from cuttings produced during drilling, said shale sample having at least two flat, parallel opposite surfaces;

(b) measurement of the transmission velocity of ultrasonic waves through the sample of step (a) under ambient conditions, (c) preparation of a mixture of water-or oil-based drilling fluid and the shale sample (a);

(d) removal, after a pre-established time, of the shale sample (a) from the mixture (c) and measurement of the ultrasonic wave transmission velocity through the sample thus removed under ambient conditions;

(e) comparison between the measurements of step (d) and those of step (b).

2. The process according to claim 1, characterized in that the drilling fluid (a) is water-based.

3. The process according to claim 1, characterized in that the measurement of the acoustic wave transmission through the sample comprises:

generating an ultrasonic pulse by means of an emitter transducer (connected to a function generator) onto a surface of the sample and recording, by means of an oscilloscope (connected to a receiver transducer) the transit time t of said pulse through the sample itself; the velocity of the acoustic pulse is given by the equation V=L/t, from the thickness of the sample L.

* * * * *